United States Patent [19]

Thelen et al.

[11] 4,141,799

[45] Feb. 27, 1979

[54] PROCESS FOR THE PURIFICATION OF HIGH-MELTING ORGANIC PRODUCTS

[75] Inventors: Bernd Thelen, Leverkusen; Hans-Walter Brandt, Odenthal; Wolfgang Auge; Karl-Werner Thiem, both of Cologne, all of Fed. Rep. of Germany

[73] Assignee: Bayer Aktiengesellschaft, Leverkusen, Fed. Rep. of Germany

[21] Appl. No.: 824,198

[22] Filed: Aug. 12, 1977

[30] Foreign Application Priority Data

Aug. 21, 1976 [DE] Fed. Rep. of Germany ....... 2637689

[51] Int. Cl.$^2$ .......................... B01D 1/22; B01D 3/14
[52] U.S. Cl. ...................................... 203/48; 203/72; 159/2 E; 159/6 W; 202/158
[58] Field of Search .............. 159/DIG. 10, DIG. 16, 159/49, 2 E, 6 W, 13 A; 203/48, 91, 72; 202/205, 158; 55/41, 43, 50, 55, 183, 193, 195, 208; 260/704, 707, DIG. 35, 378, 369, 383, 384

[56] References Cited

U.S. PATENT DOCUMENTS 3,841,381 10/1974 Dassesse ...................... 159/DIG. 10

FOREIGN PATENT DOCUMENTS 1544168 2/1970 Fed. Rep. of Germany ............. 55/195
2264922 12/1975 Fed. Rep. of Germany ............. 55/195

*Primary Examiner*—Hiram H. Bernstein
*Attorney, Agent, or Firm*—Sprung, Felfe, Horn, Lynch & Kramer

[57] ABSTRACT

The purification of high-melting organic products, such an anthraquinone and substituted anthraquinones, which is substantially free from lower-boiling impurities, by melting the product to be purified by heating, while mechanically conveying the same along a path with a screw conveyer, as for example, in a melting screw; degassing the melt at a reduced pressure in a column, as for example, at a pressure of 50 to 400 mm Hg; passing the degassed melt through a thin film evaporator at a reduced pressure of, for example, 5 to 250 mm Hg to evaporate the high-melting organic product and discharging the remaining high-boiling impurities and such impurities which are not capable of being distilled from the evaporator through a conically tapering sump, while mechanically scraping residue from the sump wall, preferably with the use of a rotating helical screw in the sump; the discharge from the sump being effected into and through an enclosed path at a rate sufficient to prevent liquid accumulating in the sump, while maintaining the central portion of the enclosed discharge path at a lower temperature than its end portion to form a crystal sludge in the central portion, which acts as a pressure seal; and solidifying and recovering the product discharging from the enclosed path. The enclosed path is preferably established through a screw-type pump which feeds into a crystallizing screw where the solidification takes place, the crystallizing screw being preferably maintained above the screw-type pump and is maintained filled with an amount of sump product which approximately corresponds to the amount of product in the sump take-off screw. The vapors produced in the thin film evaporator are passed via a heated rectifying column into a condenser, and a portion of the condensate is passed to the column as a reflux and another portion taken off and solidified in a crystallizing screw.

13 Claims, 1 Drawing Figure

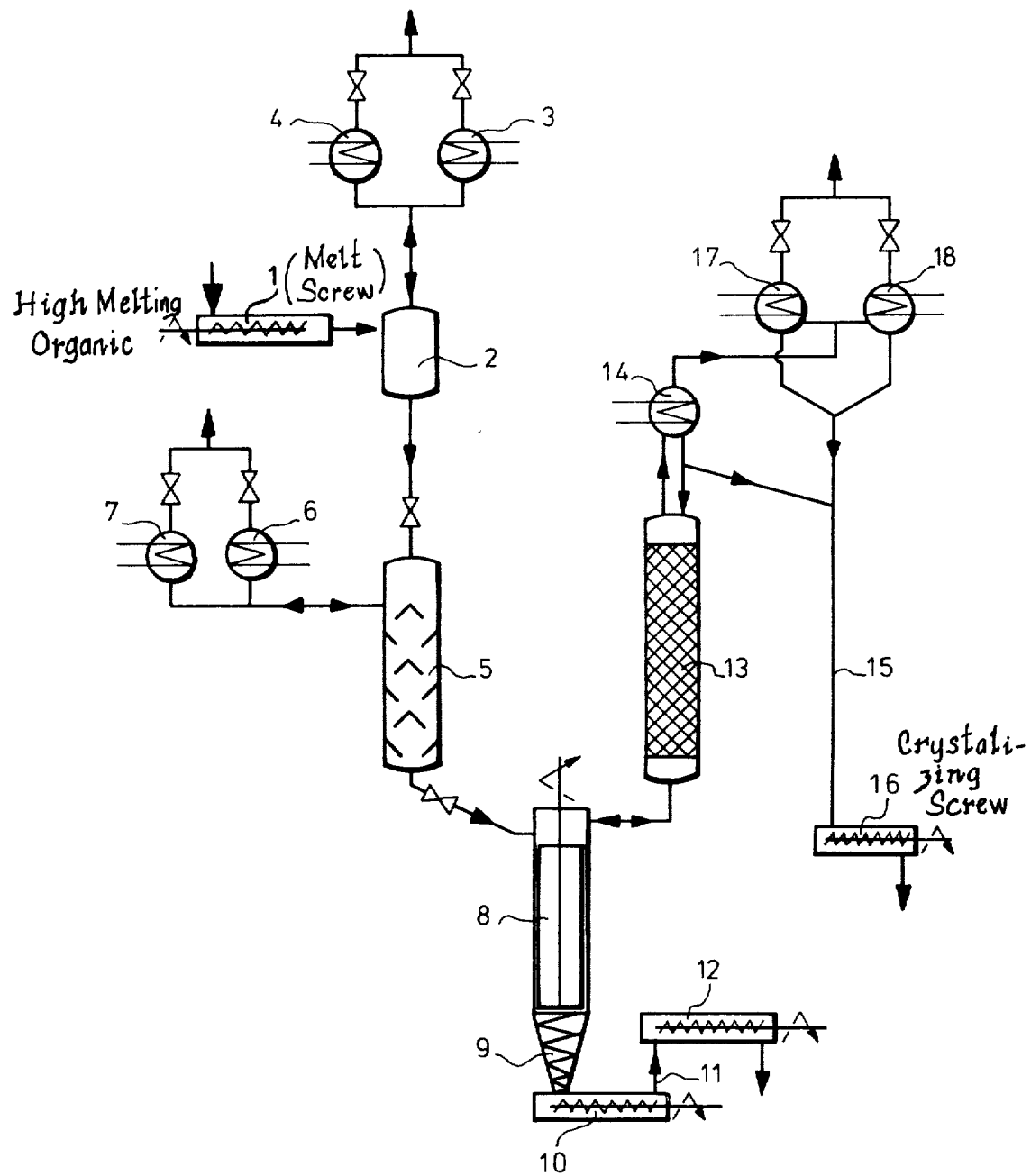

PROCESS FOR THE PURIFICATION OF HIGH-MELTING ORGANIC PRODUCTS

The present invention relates to a process for the purification of high-melting organic products.

It is known to purify high-melting organic substances, which have a sufficiently high vapour pressure, by sublimation. In the case of substances which are sensitive to heat in which case the melting point must not be exceeded for fear of decomposition of these substances sublimation can be employed to separate off impurities which do not sublime (compare Ullmanns Enzyklopädie der Technischen Chemie (Ullmanns Encyclopaedia of Industrial Chemistry), 4th edition (1972), Volume 2, page 664 et seq.). However, carrying out a sublimation necessitates a considerable technical effort and is associated with many disadvantages (compare Houben-Weyl, 4th edition (1958), Volume 1, page 931 et seq.). Thus, it is a fundamental disadvantage that during the sublimation by-products which are capable of subliming also pass over with the main product and must be separated off in a separate purification stage.

Furthermore it is known to purify fused aromatics or heterocyclic compounds which have melting points above 100° C. by evaporating the compounds, together with an inert solvent, under reduced pressure and at elevated temperature, condensing the vapours and separating the condensate into solvent and organic substance in a known manner (for this, compare DT-AS (German Published Specification) 1,245,378). However, in this process it is only possible to separate off from the substance to be purified the by-products which are not capable of being distilled. In order to separate off the by-products which are capable of being distilled, a further purification stage must be added. In addition, in this process the use of inert organic solvents gives rise to a considerable additional technical effort during the working-up of the purified substance and of the solvent.

It is also known to purify organic products with high melting points by distillation. However, special technical measures are needed if heat-sensitive substances with high melting points are to be distilled. For example, thin film evaporators with thin liquid layers or liquid films which have been produced mechanically are used for the distillation of heat-sensitive, high-boiling solutions (compare Ullmanns Enzyklopädie der Technischen Chemie (Ullmanns Encyclopaedia of Industrial Chemistry), 4th edition (1972), Volume 2, page 656 et seq.). However, in the case of a number of industrially important high-melting organic products, such as 1-nitroanthraquinone, 1-aminoanthraquinone or anthraquinone, the temperature range between the melting point and the start of the severe thermal decomposition of the product, that is to say the temperature range in which a distillation or rectification is possible, is so small that a distillation or rectification of these products has hitherto not been attempted.

In addition to the technical difficulties which occur in the rectification of high-melting organic products having a small temperature range which is suitable for the rectification, there are also objections, for reasons of safety, to rectifying or distilling nitro compounds, for example 1-nitroanthraquinone, since nitro-aromatics tend to explode under heat treatment (compare Houben-Weyl, 4th edition (1971), Volume X/I, page 479; H. Kast, Spreng- und Zündstoffe (Explosives and Detonators), Vieweg-Verlag, Brunswick (1921), page 224 et seq.; T. Urbanski, Chemistry and Technology of Explosives, Pergamon Press Book, New York (1964), page 188; and DT-OS (German Published Specification) 2,334,276).

A process has now been found for the purification of high-melting organic products, which are substantially free from more highly volatile constituents, which is characterised in that (a) the high-melting organic products to be purified are liquefied in a melting screw, (b) the melt is degassed in a column at 50 to 400 mm Hg, (c) evaporated at 5 to 250 mm Hg in a thin film evaporator with a sump outlet part which tapers conically, (d) the remaining higher-boiling impurities in the sump and such impurities, which are not capable of being distilled, are fed by means of a helical screw into a screw-type pump for the sump take-off and (e) the sump product is taken off into a crystallising screw with the aid of a screw-type pump for the sump take-off which is temperature-controlled so that a viscous crystal sludge forms in the central portion of the screw-type pump for the sump take-off, the speed of rotation of the screw-type pump for the sump take-off being adjusted so that no liquid collects in the sump outlet part of the thin film evaporator and the connection from the screw-type pump for the sump take-off and the crystallising screw is led upwards and filled with an amount of sump product which approximately corresponds to the amount of product in the sump take-off screw, (f) the vapours produced in the evaporator are passed, via a heated rectifying column, into a condenser, the condenser being heated to a temperature above the melting point of the product to be purified, and (g) some of the condensate is passed to the column as the reflux and some is taken off and solidified in a crystallising screw.

It is an essential characteristic of the process according to the invention that before the rectification of the high-melting organic products, these are freed from lower-boiling impurities by known measures, such as crystallisation, distillation or extraction.

For carrying out the process according to the invention industrially, it is important that the residence time of the high-melting organic products, which are to be purified, in the zones of the rectifying installation, where the temperature is close to the decomposition temperature of the products employed, is kept low. By this measure it is possible to keep the rate of decomposition of the high-melting organic products below 1% by weight and thus to carry out a rectification which is acceptable from the point of view of safety and, in addition, particularly high yields and, above all, high purities are achieved by means of this. Thus, purities which are over 99% by weight are achieved by the process according to the invention. The yields of high-melting organic product are 90 to 95% by weight (relative to the total substance employed which is capable of being distilled).

All higher-melting organic compounds, for example those with a melting point in the range from 100° to 300° C., can be employed in the process according to the invention. Preferably, those organic compounds which have melting points in the range from 200° to 250° C. are employed. Higher-melting organic compounds which may be mentioned which are suitable for a rectification by the process according to the invention are aromatic compounds with two or more aromatic nuclei, especially substituted aromatic compounds with two or more aromatic nuclei, for example substituted naphthalenes, anthraquinone and substituted anthraquinones, preferably 1-nitroanthraquinone, 1-aminoanthraquinone, 1-chloroanthraquinone, 1,4-dihydroxyanthraquinone and 1,5-diaminonaphthalene. 1-Nitroanthraquinone can be particularly advantageously rectified by the process according to the invention.

For carrying out the process according to the invention it is important that the entire installation is temperature-controlled by heating so that the temperature is never below the particular melting point of the product employed and, on the other hand, the temperatures at which a severe thermal decomposition of the products employed occurs are not reached or are only briefly reached.

Accordingly, the most favourable temperatures for operating the installation are in the range from 200° C. to 350° C.

It is advisable to employ heat transfer oils for heating the installation.

In order to make the rectification more economical and to achieve an improvement of yield in the rectification, all off-gases which are obtained can be passed over interchangeable cold traps which are arranged in parallel and are to be operated alternately, the organic products in the off-gases separating out. By heating up the cold traps to temperatures above the melting point of the organic products adhering to the cold traps, these products are liquefied and fed back to the particular part of the installation.

The procedure in an industrial embodiment of the process according to the invention can be as follows (for this, compare Drawing).

The organic product to be purified is fed, as poured-out material, to a self-cleaning melt screw (1). Melting of the product takes place in the screw. The melt leaves the screw and runs into a receiver (2) in which mainly gases, such as nitrogen, water vapour and the like, which enter the melting screw with the poured-out material are separated off. These gases are charged with the product to be purified according to its partial pressure. The temperature in the cold traps (3) and (4) is lowered so that the product in the gases is desublimed. In order that they may be interchanged, the cold traps are arranged in parallel so that when the solid accumulates on the cold surfaces, the solid can be melted off again by heating up the cold trap covered. From the receiver (2), the melt enters a film column (5) which is under a slight vacuum (about 50 to 40 mm Hg). The liquid is passed in thin layers over baffles and further gases and highly volatile impurities are removed from the product with the aid of the vacuum. These vapours are also passed through cold traps (6) and (7). In accordance with the vapour pressure of the product employed and the low total pressure in the film column, they are yet more heavily charged with the product than the off-gases are which enter cold traps (3) and (4). The product which is carried with these vapours is removed from the off-gas stream in the same manner as previously in cold traps (3) and (4). The melt, which is now very largely freed from gases, is fed to a thin film evaporator (8).

The thin film evaporator operates under a higher vacuum than the film column (5 to 250 mm Hg, preferably 5 to 30 mm Hg). The pressure depends on the saturation pressure which prevails at the melting point of the product employed. It is at least 1.5 times as high as this saturation pressure. Preferably, a thin film evaporator with a low-speed rotor (about 60 to 300 revolutions per minute) which is over-mounted is employed. A low-speed rotor on the one hand guarantees a high vacuum sealing of the shaft gland, and on the other hand the rotor can drive directly a helical screw in the narrow, conical outlet part of the thin film evaporator (9) without particular technical difficulty. This conical outlet part taper can be constructed in such a manner that its angle of inclination (measured with respect to the horizontal line) is, for example, between 45 and 90 degrees, preferably between 50 and 75 degrees. The helical screw prevents the higher-melting organic product which has separated out and also non-liquid cracked-products from building up on the wall of the conical outlet part of the thin film evaporator. A twin-shaft screw-type pump (10) which can be temperature-controlled in stages is located below the conical outlet part of the evaporator. The screw-type pump is heated in the inlet zone so that the sump product which drains out of the thin film evaporator via the helical screw remains essentially liquid. The central part of the screw-type pump is cooled so that a crystal sludge of a certain viscosity is present in order that the screw-type pump can build up a sufficiently high pressure to overcome the pressure difference between the external pressure (normal pressure) and the pressure in the evaporator (vacuum). The discharging zone of the screw and the outlet tube (11) are heated so that the crystal sludge produced in the screw-type pump partly melts again. Caking of crystals on the wall is thus avoided in this zone. The outlet tube (11) leads upwards. This has the result that the screw-type pump (10) always remains filled, as a shut-off of the installation to external pressure, and thus also the screw-type pump for the sump take-off remains operative when the inlet into the installation is shut off. The sump product, which essentially consists of the higher-boiling impurities, is crystallised in a crystallising screw (12), by means of cooling, and removed from the installation.

The vapours produced in the thin film evaporator (8) are passed through a low pressure-drop rectifying column (13). The length of the column depends on the severity of the separation problem. Columns of a low pressure-drop design with, at the same time, a high number of theoretical stages (for example columns having wire gauze packing or metal packing beds) can, in principle, be employed. The column must be heated adiabatically in order to compensate the heat losses and to exclude crystallising out of the product on the walls of the column. The vapours which flow out of the column (13) are condensed in the condenser (14), which is heated to above the melting point of the distillate. Some of the liquid distillate is passed into the column as the reflux and some is removed via the distillate take-off. The reflux ratio R/E (ratio of distillate reflux/distillate removal) depends on the separation conditions of the product to be purified. The removal of the distillate takes place barometrically via line (15). Under normal pressure, the distillate is crystallised in the crystallising screw (16) and removed from the installation. Because of the very low total pressure in the installation, the gases flowing through the condenser (14), which consist of air (leakage of the installation) and of cracked gases from the thermal decomposition of the product (for example $CO$ and $CO_2$), are charged to a high degree with the product to be purified since the vapour pressure of the product above its own melting point is not substantially lower than the total pressure. Thus, in accordance with the amount of gas flowing through, cold traps (17) and (18), in which the gas is freed from the product carried with it, are necessary. In a similar manner to cold traps (3) and (4) as well as (6) and (7), these cold traps are also melted off, when the cold surfaces are correspondingly heavily coated with solid, by heating up to above the melting point of the product adhering. The product which is obtained here is very pure (98 to 99%) and is drawn off, together with the actual distillate, via line (15). Because of the high melting points of the products, all the apparatuses, pipelines and fittings which come into contact with the product are provided with jackets in order to be able to keep the temperature in the apparatuses, pipelines and fittings above the melting points of the products.

The melt screw (1) and the crystallising screws (12) and (16) can be, for example, so-called "Self-cleaning Screw Heat Exchangers" as distributed by Lurgi Gesellschaft fur Warmetechnik, Frankfurt, and Maschinenfabrik B. Thies, Coesfeld. The thin film evaporator (8) can be, for example, a so-called "Rotafilm" as distributed by Canzler, Düren. The screw-type pump (10) can be, for example, a screw-pump as distributed by Leistritz GmbH, Nürnberg.

The process according to the invention has the following advantages: high-melting organic products having only a narrow temperature range between the melting point and the start of severe thermal decomposition can be purified by rectification. By short residence times of the high-melting organic products, which are to be purified, in the zones of the rectifying installation, where the temperatures are close to the decomposition temperature of the products employed, it is possible to keep the rate of decomposition during the rectification below 1% by weight. Furthermore, because of the short residence times achieved, it is possible to rectify nitroaromatics, especially nitroanthraquinone mixtures, without objections from the point of view of safety. In addition, the process according to the invention can also be carried out exceptionally economically, since the products to be purified can be subjected to the rectification without using additional auxiliaries and good yields and particularly high purities are thereby achieved, and the resulting products can be directly employed, after the rectification, for further processing.

The examples which follow are intended to illustrate the process according to the invention in more detail without limiting it, however, to these examples.

EXAMPLES

In all of the following Examples an equipment was used having following characteristics:
melting screw (1): Self-cleaning Screw Heat Exchanger as distributed by Lurgi Gesellschaft für Wärmetechnik, Frankfurt, and Maschinenfabrik B. Thies, Coesfeld. Outer diameter of screws 32 mm, core diameter of screws 24 mm, screw pitch 20 mm, profile length 540 mm. receiver (2): content 500 ml. cold traps (3) and (4): nest of vertically disposed tubes, 0,2 $m^2$ cooling face. film column (5): inner diameter 50 mm, length 500 mm. cold traps (6) and (7): nest of vertically disposed tubes, 0,5 $m^2$ cooling face. thin film evaporator (8): So-called "Rotafilm" as distributed by Canzler, Düren, 0,2 $m^2$ heating face. conical sump outlet (9): angle of inclination measured with respect to the horizontal line 60 degrees. take off screw (10): Screw pump as distributed by Leistritz GmbH, Nürnberg. Outer diameter of screws 58 mm, core diameter of screws 40 mm, screw pitch 50 mm, profile length 430 mm. line (11): diameter 50 mm. Screw (12): as screw (1), however, core diameter of screws 17 mm and profile length 400 mm. column (13): type "Sulzer Bx", inner diameter 161 mm. condenser (14): nest of vertically disposed tubes, 1,4 $m^2$ cooling face. line (15): inner diameter 21 mm screw (16): as screw (12), however, profile length 750 mm. cold traps (17) and (18): ribbed tubes, 10 $m^2$ cooling face.

EXAMPLE 1

A pre-purified and dried mixture, consisting of 0.4% by weight of anthraquinone, 0.2% by weight of 2-nitroanthraquinone, 90.2% by weight of 1-nitro-anthraquinone, 8.4% by weight of 1,5- and 1,8-dinitroanthraquinone, 0.3% by weight of 1,6- and 1,7-dinitroanthraquinone and 0.6% by weight of hydroxy-nitro- and hydroxy-dinitro-anthraquinone isomers, prepared according to DT-OS (German Published) No. 2,256,644 is melted continuously in the melting screw (1) at 215°–225° C.

The melt runs into the receiver (2) at a temperature of 250° C. From there, 10.42 kg per hour are fed into the film column (5), which is operated under a vacuum of 150 mm Hg. The film column as well as all the lines up to the thin film evaporator (8) are heated to 250° C. by tracing. The product is further passed from the film column into the thin film evaporator (8), which is heated to 310° C. The thin film evaporator and its associated installation are under a head vacuum of 10 mm Hg. The more highly volatile constituents such as anthraquinone, 2-nitro-anthraquinone and 1-nitroanthraquinone, and also some of the higher-boiling impurities are vaporised in the thin film evaporator. 1.65 kg/hour of a sump mixture of the following composition are obtained in the conical sump outlet (9): 44.0% by weight of 1-nitroanthraquinone, 52.0% by weight of 1,5- and 1,8-dinitroanthraquinone, 1.0% by weight of 1,6- and 1,7-dinitroanthraquinone, 2.0% by weight of hydroxy-nitro- and hydroxy-dinitro-anthraquinone isomers and 1.0% by weight of other substances.

The sump outlet (9) is heated to a temperature of 290° C. so that the higher-melting constituents, that is to say 1,5-dinitroanthraquinone and 1,8-dinitroanthraquinone, do not appreciably crystallise out and a condensation of 1-nitroanthraquinone is substantially prevented. The sump product contains a small proportion of product which has crystallised out as well as non-melting cracked products. It is pushed by the helical screw into the inlet part of the take-off screw (10). The inlet part of the screw is also heated to 290° C. The central zone of the screw is heated, via the outer shell, to 200° C. By this means, a crystal sludge is produced in the screw, the average viscosity of which is so high that the screw overcomes the pressure difference between 10 mm Hg and normal pressure. The outlet part of the screw and the line (11) are heated to a temperature of 260° C. so that no further crystallisation takes place on the walls and no blocking of the line by caking of the product is possible. The product crystallises in the screw (12), which is cooled with cooling water, and is removed from the installation.

The vapours produced in the evaporator (8) are rectified in a concentrating column (13). The column is packed to a height of 1.5 m and has an efficiency of about 7 theoretical plates. The column is heated adiabatically via the outer shell heating. The boiling point of the distillate at the head of the column is about 280° C.

The vapours are condensed in the condenser (14), which is heated to 235° C., that is to say above the melting point of 1-nitro-anthraquinone. The reflux ratio R/E is 0.4/1. The distillate, which is free from dinitroanthraquinone and has the following composition: 0.5% by weight of anthraquinone, 0.3% by weight of 2-nitroanthroquinone, 99.0% by weight of 1-nitroanthraquinone and 0.2% by weight of hydroxy-nitro- and hydroxy-dinitro-anthraquinone isomers, is fed barometrically to the crystallising screw (16) via line (15). The distillate lines are heated so that the temperature is above the melting point of 1-nitroanthraquinone. The screw (16), which is cooled with water, gives 8.76 kg per hour of highly pure (purity $\leq$ 99%) 1-nitroanthraquinone. The product which solidifies in the cold traps (3), (4), (6), (7), (17) and (18) essentially consists of 1-nitroanthraquinone and is melted off as necessary by heating up the particular cold trap to about 250° C. The cold trap, which is then operating in parallel in the inert gas stream, is cooled with cooling water. The total rate of decomposition is $<$ 0.5%, relative to the amount of product running in (employed).

EXAMPLE 2

A pre-purified and dried nitro-anthraquinone mixture, prepared according to DT-OS (German Published) No. 2,256,644, is converted, by replacement by ammonia under pressure, into a corresponding aminoanthraquinone mixture of the following composition: 0.8% by weight of anthraquinone, 0.2% by weight of 2-nitro-anthraquinone, 89.5% by weight of 1-aminoanthraquinone, 8.4% by weight of diamino-anthraquinones and 1.1% by weight of other substances.

About 8 kg/h of this mixture are taken up continuously by the melting screw (1) and melted at 240°–250° C. The melt runs into the receiver (2) at a temperature of 270° C. The downstream film column (5) operates at a temperature of 270° C. and under a pressure of 200 mm Hg. From the film column (5), the product enters into the thin film evaporator (8), which is heated to 325° C. by means of a heating medium. The thin film evaporator and the associated installation are under a head vacuum of 25 mm Hg. The more highly volatile constituents, such as anthraquinone, 2-nitro-anthraquinone and 1-amino-anthraquinone, apart from a 1-aminoanthraquinone content of 41% by weight in the sump outlet product, are expelled in the thin film evaporator. In the conical sump outlet (9), about 1.25 kg per hour of sump product of the following composition are obtained: 41.0% by weight of 1-amino-anthraquinone, 52.0% by weight of diamino-anthraquinones and 7.0% by weight of other substances.

The sump outlet (9) is heated to a temperature of 310° C. so that the more highly volatile 1-amino-anthraquinone is not condensed into the sump zone and so that, on the other hand, the higher-melting diaminoanthraquinones do not appreciably crystallise out. The helical screw (9) ensures that solid cracked products and crystals which have precipitated out do not adhere to the wall and form a deposit there. In the take-off screw (10), some of the sump product is crystallised at a heating medium temperature of 220° C. and is taken off under normal pressure. The temperature of the outlet is about 270° C. Complete solidification and cooling of the sump product takes place in the crystallising screw (12) by means of cooling water.

The vapours produced in the thin film evaporator are rectified in the concentrating column (13). The column is packed to a height of 1.5 m and has an efficiency of about 7 theoretical plates. To compensate the heat losses, the column is heated adiabatically. The boiling point of the distillate at the head of the column is 291° C. (25 mm Hg). The vapours are condensed in the condenser (14) at a temperature of 260° C., that is to say above the melting point of 1-amino-anthraquinone. The reflux ratio R/E is 0.3/1. The distillate, which is free from diaminoanthraquinone, has the following composition: 0.7% by weight of anthraquinone, 0.1% by weight of 2-nitro-anthraquinone, 99.0% by weight of 1-amino-anthraquinone and 0.2% by weight of other substances.

The distillate is fed to the crystallising screw (17) via the line (15). The screw (16), which is cooled with water, gives about 6.75 kg per hour of very pure 1-amino-anthraquinone (purity $\leq$ 99%). All the cold traps (3), (4), (6), (7), (17) and (18), after being correspondingly heavily coated with product, which essentially consists of 1-amino-anthraquinone, are freed from adhering product by heating up to about 270° C. The total rate of decomposition is $<$ 1% relative to the amount of product running in (employed).

EXAMPLE 3

About 12 kg/hour of a 1-chloroanthraquinone mixture of the following composition: 0.2% by weight of anthraquinone, 0.2% by weight of 2-chloro-anthraquinone, 92.4% by weight of 1-chloro-anthraquinone, 5.4% by weight of 1,5- and 1,8-dichloro-anthraquinone, 0.4% by weight of 1,6- and 1,7-dichloro-anthraquinone and 1.4% by weight of other substances, are taken up continuously by the melting screw (1) and melted at 160°–170° C. The melt runs into the receiver (2) at a temperature of 200° C. The downstream film column (5) operates at a temperature of 200° C. and under a pressure of 100 mm Hg. From the film column (5), the product enters the thin film evaporator (8), which is heated to 320° C. by means of a heating medium. The thin film evaporator and the associated installation are under a head vacuum of 25 mm Hg. The more highly volatile constituents, such as anthraquinone, 2-chloroanthraquinone and 1-chloro-anthraquinone, apart from a residual 1-chloro-anthraquinone content of 38% by weight in the sump outlet product, are expelled in the thin film evaporator. In the conical sump outlet (9), about 1.3 kg per hour of sump product of the following composition are obtained: 38.0% by weight of 1-chloroanthraquinone, 45.0% by weight of 1,5- and 1,8-dichloro-anthraquinone, 4.0% by weight of 1,6- and 1,7-dichloro-anthraquinone and 13.0% by weight of other substances.

The sump outlet (9) is heated to a temperature of 290° C. so that the more highly volatile 1-chloro-anthraquinone is not condensed into the sump zone and so that, on the other hand, the higher-melting dichloroanthraquinones do not crystallise out. The helical screw (9) ensures that solid cracked products do not adhere to the wall and form a deposit there. In the take-off screw (10), some of the sump product is crystallised at a heating medium temperature of 150° C. and is taken off under normal pressure. The temperature of the outlet (11) is about 190° C. Complete solidification and cooling of the sump product is effected in the crystallising screw (12) by means of cooling water. The vapours produced in the thin film evaporator are rectified in the concentrating column (13). The column is packed to a height of 3.5 m and has an efficiency of about 16 theoretical plates. To compensate the heat losses, the column is heated adiabatically. The boiling point of the distillate at the head of the column is 270° C. at 25 mm Hg. The vapours are condensed in the condenser (14) at a temperature of 170° C., that is to say above the melting point of 1-chloro-anthraquinone. The reflux ratio R/E is 1.5/1. The distillate of the following composition: ~ 0.2% by weight of anthraquinone, 0.2% by weight of 2-chloro-anthraquinone, 99.0% by weight of 1-chloro-anthraquinone and 0.6% by weight of dichloro-anthraquinones is fed to the crystallising screw (16) via line (15). The screw (16), which is cooled with water, gives about 10.7 kg per hour of very pure 1-chloro-anthraquinone (purity ≧ 99%). All the cold traps (3), (4), (6), (7), (17) and (18), after being correspondingly heavily coated with product, which essentially consists of 1-chloro-anthraquinone, are freed from adhering product by heating up to about 200° C. The total rate of decomposition is < 0.3%, relative to the amount of product running in (employed).

EXAMPLE 4

About 9 kg/hour of a crude 1,4-dihydroxy-anthraquinone mixture of the following composition: 92.0% by weight of 1,4-dihydroxy-anthraquinone, 2.0% by weight of 2-chloro-quinizarine, 2.0% by weight of 1,2,4-trihydroxy-anthraquinone and 4.0% by weight of other substances, are taken up continuously by the melting screw (1) and melted at a temperature of 190°-200° C. The melt runs into the receiver (2) at a temperature of 230° C. The downstream film column (5) operates at a temperature of 230° C. and under a pressure of 100 mm Hg. From the film column (5), the product enters the thin film evaporator (8), which is heated to 315° C. by means of a heating medium. The thin film evaporator and the associated installation are under a head vacuum of 20 mm Hg. The more highly volatile 1,4-dihydroxy-anthraquinone, apart from a 1,4-dihydroxy-anthraquinone content of 44% by weight in the sump outlet product, is expelled in the thin film evaporator. In the conical sump outlet (9), about 1 kg per hour of sump product of the following composition are obtained: 44.0% by weight of 1,4-dihydroxy-anthraquinone, 2.4% by weight of 2-chloro-quinizarine, 11.6% by weight of 1,2,4-trihydroxy-anthraquinone and 42.0% by weight of other substances.

The sump outlet (9) is heated to a temperature of 285° C. so that the more highly volatile 1,4-dihydroxy-anthraquinone does not condense into the sump zone and so that, on the other hand, the very viscous sump product remains capable of flow. The helical screw (9) ensures that solid cracked products and crystals which have separated out do not adhere to the wall and form a deposit there. In the take-off screw (10), some of the sump product is crystallised at a heating medium temperature of 200° C. and is taken off under normal pressure. The temperature of the outlet (11) is about 230° C. Complete solidification and cooling of the sump product takes place in the crystallising screw (12) by means of cooling water.

The vapours produced in the thin film evaporator are rectified in the concentrating column (13). The column is packed to a height of 1.5 m and has an efficiency of about 7 theoretical plates. To compensate the heat losses, the column is heated adiabatically. The boiling point of the distillate at the head of the column is 270° C. at 20 mm Hg. The vapours are condensed in the condenser (14) at a temperature of 210° C., that is to say above the melting point of 1,4-dihydroxy-anthraquinone. The reflux ratio R/E is 0.5/1. The distillate of the following composition: 98.0% by weight of 1,4-dihydroxy-anthraquinone, 0.2% by weight of 2-chloro-quinizarine, 0.8% by weight of 1,2,4-trihydroxy-anthraquinone and 1.0% by weight of other substances, is fed to the crystallising screw (16) via line (15). The screw (16), which is cooled with water, gives about 8 kg per hour of very pure 1,4-dihydroxy-anthraquinone (purity ≧ 98%). All the cold traps (3), (4), (6), (7), (17) and (18), after being correspondingly heavily coated with product, which essentially consists of 1,4-dihydroxy-anthraquinone, are freed from adhering product by heating up to about 220° C. The total rate of decomposition is < 0.2%, relative to the amount of product running in (employed).

EXAMPLE 5

About 6 kg/hour of a crude anthraquinone mixture of the following composition: 0.2% by weight of lower-boiling constituents, 91.0% by weight of anthraquinone, 5.0% by weight of higher-boiling constituents and 4.8% by weight of other substances, are taken up continuously by the melting screw (1) and melted at 280°-290° C. The melt runs into the receiver (2) at a temperature of 310° C. The downstream film column (5) operates at a temperature of 310° C. and under 350 mm Hg. From the film column (5), the product enters the thin film evaporator (8), which is heated to 360° C. by means of a heating medium. The thin film evaporator and the associated installation are under a head vacuum of 250 mm Hg. The more highly volatile anthraquinone, apart from an anthraquinone content of 46% by weight in the sump product, is expelled in the thin film evaporator. In the conical sump outlet (9), about 1 kg per hour of sump product of the following composition are obtained: 46.0% by weight of anthraquinone, 30.0% by weight of higher-boiling constituents and 24.0% by weight of other substances.

The sump outlet (9) is heated to a temperature of 340° C. so that the more highly volatile anthraquinone is not condensed into the sump zone and so that, on the other hand, the viscous sump product remains capable of flow. The helical screw (9) ensures that solid cracked products and crystals which have separated out do not adhere to the wall and form a deposit there. In the take-off screw (10), some of the sump product is crystallised at a heating medium temperature of 270° C. and is taken off under normal pressure. The temperature of the outlet (11) is about 300° C. Complete solidification and cooling of the sump product takes place in the crystallising screw (12) by means of cooling water.

The vapours produced in the thin film evaporator are rectified in the concentrating column (13). The column is packed to a height of 1.5 m and has an efficiency of about 7 theoretical plates. To compensate the heat losses, the column is heated adiabatically. The boiling point of the distillate at the head of the column is 324° C. at 250 mm Hg. The vapours are condensed in the condenser (14) at a temperature of 290° C., that is to say above the melting point of anthraquinone. The reflux ratio R/E is 0.2/1. The anthraquinone, which is 99.6% by weight pure, is fed, as the distillate, to the crystallising screw (16) via line (15). The screw (16), which is cooled with water, gives abut 5 kg per hour of very pure anthraquinone. All the cold traps (3), (4), (6), (7), (17) and (18), after being correspondingly heavily coated with product, which essentially consists of anthraquinone, are freed from adhering product by heating up to about 300° C. The total rate of decomposition is < 1%, relative to the amount of product running in (employed).

EXAMPLE 6

About 9 kg/hour of a crude 1,5-diaminonaphthalene mixture of the following composition: 93.4% by weight of 1,5-diaminonaphthalene, 0.8% by weight of 1-naphthylamine, 0.8% by weight of purpurole and 5.0% by weight of other substances, are taken up continuously by the melting screw (1) and melted at a temperature of 190°–200° C. The melt runs into the receiver (2) at a temperature of 230° C. The downstream film column (5) operates at a temperature of 230° C. and under a pressure of 100 mm Hg. From the film column (5), the product enters the thin film evaporator (8), which is heated to 305° C. by means of a heating medium. The thin film evaporator and the associated installation are under a head vacuum of 40 mm Hg. The more highly volatile 1,5-diaminonaphthalene apart from a 1,5-diaminonaphthalene content of 40% by weight in the sump outlet product, is expelled in the thin film evaporator. In the conical sump outlet (9), about 0.85% kg per hour of sump product of the following composition are obtained: 40.0% by weight of 1,5-diaminonaphthalene, 0.2% by weight of 1-naphthylamine, 8.5% by weight of purpurole and 51.3% by weight of other substances.

The sump oullet (9) is heated to a temperature of 275° C. so that the more highly volatile 1,5-diaminonaphthalene does not condense into the sump zone and so that, on the other hand, the viscous sump product remains capable of flow. The helical screw (9) ensures that solid cracked products and crystals which have separated out do not adhere to the wall and form a deposit there. In the take-off screw (10), some of the sump product is crystallised at a heating medium temperature of 190° C. and is taken off under normal pressure. The temperature of the outlet (11) is about 230° C. Complete solidification and cooling of the sump product takes place in the crystallising screw (12) by means of cooling water.

The vapours produced in the thin film evaporator are rectified in the concentrating column (13). The column is packed to a height of 1.5 m and has an efficiency of about 7 theoretical plates. To compensate the heat losses, the column is heated adiabatically. The boiling point of the destillate at the head of the column is 265° C. at 40 mm Hg. The vapours are condensed in the condenser (14) at a temperature of 195° C., that is to say above the melting point of 1,5-diaminonaphthalene. The reflux ration R/E is 0.5/1. The distillate of the following composition: 99% by weight of 1,5-diaminonaphthalene, 0.9% by weight of 1-naphthylamine, below 0.1% by weight of purpurole and 0.1% by weight of other substances, is fed to the crystallising screw (16) via line (15). The screw (16), which is cooled with water, gives about 8.15 kg per hour of very pure 1,5-diaminonaphthalene (purity ≧ 99%). All the cold traps (3), (4), (6), (7), (17) and (18), after being correspondingly heavily coated with product, which essentially consists of 1,5-diaminonaphthalene are freed from adhering product by heating up to about 220° C. The total rate of decomposition is < 0.1%, relative to the amount of product running in (employed).

What is claimed is:

1. Process for the purification of high-melting organic products, which comprises (a) melting the product to be purified by heating, while mechanically conveying the same along a path with a screw conveyer,
(b) degassing the melt at a reduced pressure in a column,
(c) passing the degassed melt through a thin film evaporator at a reduced pressure to evaporate the high-melting organic product, passing the vapors produced in the thin film evaporator through a rectifying column and discharging the remaining high-boiling impurities and such impurities which are not capable of being distilled from the evaporator through a conically tapering sump, while mechanically scraping residue from the sump wall,
(d) said discharging being effected into and through an enclosed path at a rate sufficient to prevent liquid accumulation in the sump, while maintaining the central portion of the enclosed discharge path at a lower temperature than its end portions to form a crystal sludge in this central portion, which acts as a pressure seal, and
(e) solidifying and recovering the product discharging from said path.

2. Process according to claim 1, in which (b) is effected at a pressure of 50 to 400 mm Hg, and (c) is effected at a pressure of 5 to 250 mm Hg.

3. Process according to claim 1, in which (a) is effected in a melting screw.

4. Process according to claim 1, in which the conically tapering sump of the thin film evaporator is provided with a rotating helical screw, and in which said enclosed path is defined through a screw-type pump for the sump take-off.

5. Process according to claim 4, in which (e) is effected by leading the discharge from the screw-type pump upwardly and through a crystallizing screw filled with an amount of the sump product which approximately corresponds to the amount of product in the screw-type pump for the sump take-off.

6. Process according to claim 1, in which the vapors produced in the thin film evaporator are passed through the heated rectifying column into a condenser, and in which a portion of the condensate is refluxed to the column and another portion removed and solidified in a crystallizing screw.

7. Process according to claim 1, in which said high-melting organic product to be purified is a product having a melting point between 100° and 300° C. and which is substantially free of more highly volatile components.

8. Process according to claim 7, in which said high-melting organic product to be purified is a member selected from the group consisting of aromatic and substituted aromatic compounds with two or more aromatic nuclei.

9. Process according to claim 8, in which said high-melting organic product is selected from the group consisting of 1-nitro-anthraquinone, 1-aminoanthraquinone, 1-chloroanthraquinone, 1,4-dihydroxy-anthraquinone and 1,5-diaminonaphthalene.

10. Process according to claim 9, in which said high-melting organic product is 1-nitro-anthraquinone.

11. Process according to claim 1, which includes cooling the gases produced in the process to solidify at least a portion thereof, heating the solid formed to cause its liquefaction and recycling the same.

12. Process according to claim 1, in which the temperature in steps (a) through (c) is maintained at at least the melting point of the product and not substantially in excess of the temperature at which substantial thermal decomposition of the product occurs.

13. An apparatus which comprises (a) means for heating and conveying a product to be purified along a path, wherein said means comprises a screw conveyor, (b) a column receptive of the melt for degassing said melt at a reduced pressure, (c) a thin film evaporater through which the degassed melt is passed at a reduced pressure to evaporate the high melting organic product, (d) a rectifying column receptive of the high melting organic product vapors produced in the thin film evaporater, (e) a conically tapering sump for discharging the remaining high boiling impurities and such impurities which are not capable of being stilled from the evaporater, (f) means defining an enclosed path for receiving the discharge at a rate sufficient to prevent liquid accumulation in the sump, while maintaining to form a crystal sludge in the central portion which acts as a pressure seal and (g) means for solidifying and recovering the product discharging from said path.

* * * * *

UNITED STATES PATENT AND TRADEMARK OFFICE
CERTIFICATE OF CORRECTION

PATENT NO. : 4,141,799
DATED : February 27, 1979
INVENTOR(S) : Bernd Thelen, et al.

It is certified that error appears in the above-identified patent and that said Letters Patent are hereby corrected as shown below:

Column 3, line 50, "40" should be --400--

Column 8, line 17, " $\leq$ " should be -- $>$ --

Signed and Sealed this

Twelfth Day of June 1979

[SEAL]

Attest:

RUTH C. MASON
*Attesting Officer*

DONALD W. BANNER
*Commissioner of Patents and Trademarks*